(12) United States Patent
Patel et al.

(10) Patent No.: US 11,278,521 B2
(45) Date of Patent: Mar. 22, 2022

(54) GAS5 BINDING COMPOUNDS, FORMULATIONS, AND USES THEREOF

(71) Applicants: UNIVERSITY OF SOUTH FLORIDA, Tampa, FL (US); The United States Government as Represented by The Department of Veterans Affairs, Washington, DC (US)

(72) Inventors: Niketa A. Patel, Tampa, FL (US); Jianfeng Cai, Tampa, FL (US)

(73) Assignees: UNIVERSITY OF SOUTH FLORIDA, Tampa, FL (US); THE UNITED STATES GOVERNMENT AS REPRESENTED BY THE DEPARTMENT OF VETERANS AFFAIRS OFFICE OF GENERAL COUNSEL—PSG IV (024), Washington, DC (US)

( * ) Notice: Subject to any disclaimer, the term of this patent is extended or adjusted under 35 U.S.C. 154(b) by 743 days.

(21) Appl. No.: 16/063,077

(22) PCT Filed: Dec. 15, 2016

(86) PCT No.: PCT/US2016/066937
§ 371 (c)(1),
(2) Date: Jun. 15, 2018

(87) PCT Pub. No.: WO2017/106505
PCT Pub. Date: Jun. 22, 2017

(65) Prior Publication Data
US 2021/0198221 A1    Jul. 1, 2021

Related U.S. Application Data

(60) Provisional application No. 62/398,624, filed on Sep. 23, 2016, provisional application No. 62/267,650, filed on Dec. 15, 2015.

(51) Int. Cl.
| | | |
|---|---|---|
| *A61K 31/396* | (2006.01) | |
| *A61K 31/395* | (2006.01) | |
| *A61K 45/06* | (2006.01) | |
| *C07D 285/00* | (2006.01) | |

(52) U.S. Cl.
CPC ............ *A61K 31/395* (2013.01); *A61K 45/06* (2013.01); *C07D 285/00* (2013.01)

(58) Field of Classification Search
CPC .................................................. C07D 285/00
USPC ...................................................... 514/183
See application file for complete search history.

(56) References Cited

U.S. PATENT DOCUMENTS

2006/0275213 A1   12/2006  Bergman et al.
2014/0018302 A1   1/2014   Walensky et al.

FOREIGN PATENT DOCUMENTS

WO    2015112806 A2    7/2015

OTHER PUBLICATIONS

Colosia, Ann D, et al., "Prevalence of hypertension and obesity in patients with type 2 diabetes mellitus in observational studies: a systematic literature Review", Diabetes, metabolic Syndrome and Obesity: Targets and Therapy, 2013, pp. 327-338, vol. 6, Dovepress, doi: 10.2147/DMSO.S51325.
Raj, Srilakshmi M., et al., "Variation at Diabetes- and Obesity-Associated Loci May Mirror Neutral Patterns of Human Population Diversity and Diabetes Prevalence in India", Annals of human genetics, 2013, pp. 392-408, vol. 77, John Wiley & Sons Ltd/ University College London, doi: 10.1111/ahg.12028.
Sundborn, Gerhard, et al., "Overweight and obesity prevalence among adult Pacific peoples and Europeans in the Diabetes Heart and Health Study (DHAHS) 2002-2003, Auckland New Zealand", The New Zealand Medical Journal, 2010, pp. 1-105, vol. 123, No. 1311, New Zealand Medical Association, ISSN 11758716, url: http://www.nzma.org.nz/journal/123-1311/4038/.
Crawford, Albert G., et al, "Prevalence of Obesity,TypeII Diabetes Mellitus, Hyperlipidemia, and Hypertension in the UnitedStates: Findings from the GE Centricity Electronic Medical Record Database", Population Health Management, 2010, pp. 151-161, vol. 13, No. 3, Mary Ann Liebert, Inc., doi: 10.1089/pop.2009.0039.
Xu, X. Julia, et al., "What distinguishes adipose tissue of severely obese humans who are insulin sensitive and Resistant?", Current Opinion in Lipidology, 2013, pp. 49-56 (1-14), vol. 24, No. 1, Wolters Kluwer Health | Lippincott Williams & Wilkins, doi: 10.1097/MOL.0b013e32835b465b.
Chen, Xing, et al., "Novel human lncRNA-disease association inference based on lncRNA expression Profiles", Bioinformatics, 2013, pp. 2617-2624, vol. 29, No. 20, Oxford University Press & Advance Access, doi: 10.1093/bioinformatics/btt426.
Arase, Mayu, et al., "Transforming growth factor-b-induced lncRNA-Smad7 inhibits apoptosis of mouse breast cancer JygMC(A) Cells", Cancer Science, 2014, pp. 974-982, vol. 105, No. 8, Wiley Publishing Asia Pty Ltd on behalf of Japanese Cancer Association, doi: 10.1111/cas.12454.
Liu, Qian, et al., "LncRNA loc285194 is a p53-regulated tumor Suppressor", Nucleic Acids Research, 2013, pp. 4976-4987, vol. 41, No. 9, Oxford University Press, doi: 0.1093/nar/gkt182.
Amaral, Paulo P., et al., "LncRNAdb: a reference database for long noncoding RNAs", Nucleic acids Research, 2011, pp. D146-D151, vol. 39, Oxford University Press, doi: 10.1093/nar/gkq1138.
Williams, Gwyn T., et al., "A critical role for non-coding RNA GAS5 in growth arrest and rapamycin inhibition in human T-Lymphocytes", Biochemical Society Transactions, 2011, pp. 482-486, vol. 39, No. 2, Biochemical Society, doi: 10.1042/BST0390482.
Budczies, Jan, et al., "Cutoff Finder: A Comprehensive and Straightforward Web Application Enabling Rapid Biomarker Cutoff Optimization", PLOS One, 2012, pp. 1-7, vol. 7, No. 12, doi: 10.1371/ journal.pone.0051862.
Taneera, Jalal, et al., "Identification of novel genes for glucose metabolism based upon expression pattern in human islets and effect on insulin secretion and Glycemia", Human Molecular Genetics, 2015, pp. 1945-1955, vol. 24, No. 7, Oxford University Press & Advance Access, doi: 10.1093/hmg/ddu610.

(Continued)

*Primary Examiner* — Taofiq A Solola

(57) ABSTRACT

Provided herein are compounds that can bind GAS5 long non-coding RNA, compositions thereof, and uses thereof.

10 Claims, 4 Drawing Sheets

Specification includes a Sequence Listing.

(56) References Cited

OTHER PUBLICATIONS

Fadista, João, et al., "Global genomic and transcriptomic analysis of human pancreatic islets reveals novel genes influencing glucose Metabolism", Proceedings of the National Academy of Sciences of the United States of America (PNAS), 2014, pp. 13924-13929, vol. 111, No. 38, doi: 10.1073/pnas.1402665111.
Ding, Guo-Lian, et al., "Transgenerational Glucose Intolerance With Igf2/H19 Epigenetic Alterations in Mouse Islet Induced by Intrauterine Hyperglycemia", Diabetes, 2012, pp. 1133-1142, vol. 61, American Diabetes Association, doi: 10.2337/db11-1314.
Pasmant, Eric, et al., "ANRIL, a long, noncoding RNA, is an unexpected major hotspot in GWAS", The FASEB Journal, 2010, pp. 444-448, vol. 25, FASEB, doi: 10.1096/fj.10-172452.
Divoux, Adeline, et al., "Identification of a Novel lncRNA in Gluteal Adipose Tissue and Evidence for Its Positive Effect on Preadipocyte Differentiation", Obesity, 2014, pp. 1781-1785, vol. 22, No. 8, doi: 10.1002/oby.20793.
Cooper, Denise R., et al., "Long Non-Coding RNA NEAT1 Associates with SRp40 to Temporally Regulate PPARγ2 Splicing during Adipogenesis in 3T3-L1 Cells", Genes, 2014, pp. 1050-1063, vol. 5, Open Access, doi: 10.3390/genes5041050.
Pickard, Mark R., et al., "Regulation of apoptosis by long noncoding RNA GAS5 in breast cancer cells: implications for Chemotherapy", Breast Cancer Research and Treatment, 2014, pp. 359-370, vol. 145, Springer, doi: 10.1007/s10549-014-2974-y.
Pickard, M.R., et al., "Long non-coding RNA GAS5 regulates apoptosis in prostate cancer cell Lines", Biochimica et Biophysica Acta, 2013, pp. 1613-1623, vol. 1832, Elsevier B.V., doi: 10.1016/j.bbadis.2013.05.005.
Mourtada-Maarabouni, M., et al., "GAS5, a non-protein-coding RNA, controls apoptosis and is downregulated in breast Cancer", Oncogene, 2009, pp. 195-208, vol. 28, Macmillan Publishers Limited, www.nature.com/onc.
Huang, Xiaoyi, et al., "Characterization of human plasma-derived exosomal RNAs by deep Sequencing", BMC Genomics, 2013, pp. 1-14, vol. 14, No. 319, BioMed Central Ltd & Open Access, http://www.biomedcentral.com/1471-2164/14/319.
Tsui, Nancy B. Y., et al., "Molecular Analysis of Circulating RNA in Plasma", Methods in Molecular Biology, editors: Lo, Y. M. Dennis, et al., pp. 123-134, vol. 336: Clinical Applications of PCR, 2nd ed. Humana Press Inc., ISSN 1064-3745, doi: 10.1385/1-59745-074-X:123.
Wang, Kai, et al., "The Spectrum of Circulating RNA: A Window into Systems Toxicology", Toxicology Sciences, 2013, pp. 478-492, vol. 132, No. 2, Oxford University Press on behalf of the Society of Toxicology, doi: 10.1093/toxsci/kft014.
Baraniskin, Alexander, et al., "Circulating U2 small nuclear RNA fragments as a novel diagnostic biomarker for pancreatic and colorectal Adenocarcinoma", International Journal of Cancer, 2013, pp. E48-E57, vol. 132, doi: 10.1002/jc.27791.
Payne, RE, et al., "Viable circulating tumour cell detection using multiplex RNA in situ hybridisation predicts progression-free survival in metastatic breast cancer Patients", British Journal of Cancer, 2012, pp. 1790-1797, vol. 106, Cancer Research UK, doi: 10.1038/bjc.2012.137.
Xie, Jianling, et al., "The role of mammalian target of rapamycin (mTOR) in the regulation of pancreatic b-cell mass implications in the development of type-2 Diabetes", Cellular and Molecular Life Sciences, 2012, pp. 1289-1304, vol. 69, Springer Basel AG, doi: 10.1007/s00018-011-0874-4.
Öst, Anita, et al., "Attenuated mTOR Signaling and Enhanced Autophagy in Adipocytes from Obese Patients with Type 2 Diabetes", Molecular Medicine, 2010, pp. 235-246, vol. 16, No. 7-8, The Feinstein Institute for Medical Research, doi: 10.2119/molmed.2010.00023.
Fraenkel, Meray, et al., "mTOR Inhibition by Rapamycin Prevents β-Cell Adaptation to Hyperglycemia and Exacerbates the Metabolic State in Type 2 Diabetes", Diabetes, 2008, pp. 945-957, vol. 57, American Diabetes Association, doi: 10.2337/db07-0922.
Lander, Eric S., et al., "Initial sequencing and analysis of the human Genome", Nature, 2001, pp. 860-921, vol. 409, Macmillian Magazines Ltd., doi: 10.1038/35057062.
Yacqub-Usman, Kiren, et al., "Reciprocal regulation of GAS5 lncRNA levels and mTOR Inhibitor", Prostate, 2015, pp. 1-32, vol. 7, doi: 10.1002/pros.22952.
International Search Report for PCT/US2016066937 dated Mar. 17, 2017.
Shi, Y., Parag, S., Patel, R., Lui, A., Murr, M., Cai, J., & Patel, N. A. (2019). Stabilization of lncRNA GAS5 by a small molecule and its implications in diabetic adipocytes Cell chemical biology, 26(3), 319-330.

SEQUENCE LISTING

```
<160> NUMBER OF SEQ ID NOS: 2

<210> SEQ ID NO 1
<211> LENGTH: 651
<212> TYPE: DNA
<213> ORGANISM: Artificial Sequence
<220> FEATURE:
<223> OTHER INFORMATION: GAS5 lncRNA

<400> SEQUENCE: 1
tttcgaggta ggagtcgact cctgtgaggt atggtgctgg gtgcggatgc agtgtggctc      60
tggatagcac cttatggaca gttgtgtccc caaggaagga tgagaatagc tactgaagtc     120
ctaaagagca agcctaactc aagccattgg cacacaggca ttagacagaa agctggaagt     180
tgaaatggtg gagtccaact tgcctggacc agcttaatgg ttctgctcct ggtaacgttt     240
ttatccatgg atgacttgct tgggtaagga catgaagaca gttcctgtca tacctttaa      300 aggtatggag agtcggcttg actacactgt gtggagcaag ttttaaagaa gcaaaggact     360
cagaattcat gattgaagaa atgcaggcag acctgttatc ctaaactagg gtttttaatg     420
accacaacaa gcaagcatgc agcttactgc ttgaaagggt cttgcctcac ccaagctaga     480
gtgcagtggc ctttgaagct tactacagcc tcaaacttct gggctcaagt gatcctcagc     540
ctcccagtgg tctttgtaga ctgcctgatg gagtctcatg gcacaagaag attaaaacag     600
tgtctccaat tttaataaat ttttgcaatc caaaaaaaaa aaaaaaaaaa a              651

<210> SEQ ID NO 2
<211> LENGTH: 111
```

```
<212> TYPE: DNA
<213> ORGANISM: Artificial Sequence
<220> FEATURE:
<223> OTHER INFORMATION: a binding sequence for a oligonucleotide probe
      in GAS5 lncRNA

<400> SEQUENCE: 2
ctcccagtgg tctttgtaga ctgcctgatg gagtctcatg gcacaagaag attaaaacag       60
tgtctccaat tttaataaat ttttgcaatc caaaaaaaaa aaaaaaaaaa a               111
```

GAS5 BINDING COMPOUNDS, FORMULATIONS, AND USES THEREOF

CROSS-REFERENCE TO RELATED APPLICATIONS

This application is the U.S. National Stage Application under 35 U.S.C. § 371 of Patent Cooperation Treaty Application No.: PCT/US16/066937, filed on Dec. 15, 2016, entitled "GAS5 BINDING COMPOUNDS, FORMULATIONS, AND USES THEREOF," the contents of which is incorporated by reference herein in its entirety.

Patent Cooperation Treaty Application No.: PCT/US16/066937 claims the benefit of and priority to U.S. Provisional Patent Application No. 62/267,650, filed on Dec. 15, 2015, entitled "GAS5-BINDING SMALL MOLECULE FOR TREATMENT OF DIABETES AND CANCER," the contents of which is incorporated by reference herein in its entirety.

Patent Cooperation Treaty Application No.: PCT/US16/066937 also claims the benefit of and priority to U.S. Provisional Patent Application No. 62/398,624, filed on Sep. 23, 2016, entitled "GAS5 BINDING COMPOUNDS, FORMULATIONS, AND USES THEREOF," the contents of which is incorporated by reference herein in its entirety.

STATEMENT REGARDING FEDERALLY SPONSORED RESEARCH OR DEVELOPMENT

This invention was made with government support under Grant Number 821-MR-EN-20606 awarded by the U.S. Department of Veterans Affairs. The government has certain rights to the invention.

SEQUENCE LISTING

This application contains a sequence listing filed in electronic form as an ASCII.txt file entitled 292103-2650_5 T25 created on Dec. 15, 2016. The content of the sequence listing is incorporated herein in its entirety.

BACKGROUND

Diabetes mellitus is a complex and costly disease that is increasing in prevalence worldwide. In 2012, it was estimated that diabetes costs the nation $245 billion, a 41% increase from costs incurred in 2007 (ADA study "Economic Costs of Diabetes in the US in 2012"). According to the American Diabetes Association (ADA), about 9.3% of the United States population is diagnosed with diabetes. Diabetes remains the seventh leading cause of death in the United States and caused about 69,000 deaths in 2010. Diabetes was listed as a contributing factor or underlying cause of an additional 234,000 deaths in 2010.

Despite increased awareness, treatments, and management approaches, diabetes not only remains a significant health issue, but the incidence of diabetes is on the rise. As such, there exists a need for improved diagnostic, treatment, and management methods for diabetes.

SUMMARY

Provided herein are compounds that can have a structure according to Formula 1, wherein $R_1$ can be a methyl, an isobutane, a phenyl, an indole, or a butanamine, wherein $R_2$ can be an ethylbenzene, an ethylcyclohexane, an isopentane, a phenyl, a propanamine, or a methylcyclopropane, wherein $R_3$ can be a methylcyclopropane, a propionic acid, an ethylbenzene, or a propanamine, wherein $R_4$ can be a butanamine, a propionic acid, or a phenyl, wherein $R_5$ can be a methylcyclopropane, a propionic acid, or an ethylbenzene, wherein $R_6$ can be a phenyl, a propionic acid, an isobutene, and wherein $R_7$ can be a phenyl, a propionic acid, a butanamine, or a methyl. The compounds with a structure according to Formula 1 can be capable of binding GAS5 long non-coding RNA. The GAS5 long non-coding RNA can have a sequence about 90%-100% identical to SEQ ID NO: 1. In some embodiments, the compound can have a structure according to any one of Formulas 3-19.

In some embodiments, the compounds can have a structure according to Formula 2, wherein $R_1$ can be an isobutane, a phenyl, an indole, or a butanamine, wherein $R_2$ can be an ethylbenzene, an ethylcyclohexane, an isopentane, a phenyl, or a propanamine, wherein $R_3$ can be a methylcyclopropane, a propionic acid, or an ethylbenzene, wherein $R_5$ can be a methylcyclopropane, a propanamine, or an ethylbenzene, wherein $R_6$ can be a phenyl, a propionic acid, an isobutene, and wherein $R_7$ can be a phenyl, a propionic acid, a butanamine, or a methyl. In some embodiments, the compound can have a structure according to any one of Formulas 3, 4, 5, 6, 7, 8, 9, 10, 11, 12, 13, 15, 16, or 19.

In some embodiments, the compounds have a structure according to Formula 20 wherein $R_1$ can be an isobutene, a phenyl, or an indole, and wherein $R_2$ can be an ethylbenzene, a phenyl, an isobutene, or a propanamine. In some embodiments, the compound can have a structure according to any one of Formulas 3, 4, 5, 6, 7, 8, 9, 10, 11, 12, or 13.

In some embodiments, the compounds have a structure according to Formula 21, wherein $R_1$ can be an isobutene, a phenyl, an indole, or a methyl, wherein $R_2$ can be an ethylbenzene, a phenyl, an isobutene, a propanamine, or an ethylcyclohexane, wherein $R_3$ can be a methylcyclopropane or a propionic acid, and wherein $R_4$ can be a butanamine or a propionic acid. In some embodiments, the compound can have a structure according to any one of Formulas 3, 4, 5, 6, 7, 8, 9, 10, 11, 12, 13, or 14.

In some embodiments, the compounds have a structure according to Formula 22, wherein $R_1$ can be an isobutene, a phenyl, an indole, or a methyl, wherein $R_2$ can be an ethylbenzene, a phenyl, an isobutene, a propanamine, an ethylcyclohexane, or a methylcyclopropane, wherein $R_3$ can be a methylcyclopropane, propionic acid, ethylbenzene, or a propanamine, wherein $R_4$, can be a butanamine or a propionic acid, and wherein $R_5$ can be a methylcyclopropane and ethylbenzene. In some embodiments, the compound can have a structure according to any one of Formulas 3, 4, 5, 6, 7, 8, 9, 10, 11, 12, 13, 14, 17, or 18.

In some embodiments, the compounds have a structure according to Formula 23, wherein $R_1$ can be an isobutene, a phenyl, an indole, or a methyl, wherein $R_2$ can be an ethylbenzene, a phenyl, an isobutene, a propanamine, or an ethylcyclohexane, wherein $R_3$ can be a methylcyclopropane or a propanamine, wherein $R_4$ can be a butanamine or a propionic acid, and wherein $R_5$ can be a methyl cyclopropane or an ethylbenzene. In some embodiments, the compound can have a structure according to any one of Formulas 3, 4, 5, 6, 7, 8, 9, 10, 11, 12, 13, 14, or 18.

Also provided herein are pharmaceutical formulations that can include a compound that can have a structure according to Formula 1, wherein $R_1$ can be a methyl, an isobutane, a phenyl, an indole, or a butanamine, wherein $R_2$ can be an ethylbenzene, an ethylcyclohexane, an isopentane, a phenyl, a propanamine, or a methylcyclopropane, wherein $R_3$ can be a methylcyclopropane, a propionic acid, an ethylbenzene, or a propanamine, wherein $R_4$ can be a butanamine, a propionic acid, or a phenyl, wherein $R_5$ can be a methylcyclopropane, a propionic acid, or an ethylbenzene, wherein $R_6$ can be a phenyl, a propionic acid, an isobutene, and wherein $R_7$ can be a phenyl, a propionic acid, a butanamine, or a methyl. and a pharmaceutically acceptable carrier. In some embodiments the compound can have a structure according to any one of formulas 3-19. The compound can be capable of binding GAS5 long non-coding RNA. The GAS5 long non-coding RNA can have a sequence about 90%-100% identical to SEQ ID NO: 1. The pharmaceutical formulation can optionally include an agent selected from the group of: antisense or RNA interference molecules, chemotherapeutics, antineoplasic agents, hormones, antibiotics, antivirals, immunomodulating agents, antinausea, pain modifying agents, anti-inflammatory agents, antipyretics, antibiotics, and/or antibodies or fragments thereof. The pharmaceutical formulation can be adapted for oral, rectal, intraocular, inhaled, intranasal, topical, vaginal, parenteral, subcutaneous, intramuscular, intravenous, or intradermal administration to a subject.

Also provided herein are kits containing a compound that can have a structure according to Formula 1, wherein $R_1$ can be a methyl, an isobutane, a phenyl, an indole, or a butanamine, wherein $R_2$ can be an ethylbenzene, an ethylcyclohexane, an isopentane, a phenyl, a propanamine, or a methylcyclopropane, wherein $R_3$ can be a methylcyclopropane, a propionic acid, an ethylbenzene, or a propanamine, wherein $R_4$ can be a butanamine, a propionic acid, or a phenyl, wherein $R_5$ can be a methylcyclopropane, a propionic acid, or an ethylbenzene, wherein $R_6$ can be a phenyl, a propionic acid, an isobutene, and wherein $R_7$ can be a phenyl, a propionic acid, a butanamine, or a methyl, and instructions printed on or otherwise contained in a tangible medium of expression. The instructions can specify the indication of use to be for treatment of diabetes, obesity, a neurodegenerative disease, a cancer, or a symptom thereof. The cancer can be breast cancer, renal clear cell cancer, bladder cancer, hepatocellular cancer, gastric cancer, cervical cancer, non-small-cell lung cancer, pancreatic cancer, malignant pleural mesothelioma, or colorectal cancer.

Also provided herein are methods of treating a disease or disorder or a symptom thereof in a subject in need thereof, where the method includes administering an amount of a compound that can have a structure according to Formula 1 or a pharmaceutical formulation that can include a compound that can have a structure according to Formula 1 to a subject in need thereof, wherein $R_1$ can be a methyl, an isobutane, a phenyl, an indole, or a butanamine, wherein $R_2$ can be an ethylbenzene, an ethylcyclohexane, an isopentane, a phenyl, a propanamine, or a methylcyclopropane, wherein $R_3$ can be a methylcyclopropane, a propionic acid, an ethylbenzene, or a propanamine, wherein $R_4$ can be a butanamine, a propionic acid, or a phenyl, wherein $R_5$ can be a methylcyclopropane, a propionic acid, or an ethylbenzene, wherein $R_6$ can be a phenyl, a propionic acid, an isobutene, and wherein $R_7$ can be a phenyl, a propionic acid, a butanamine, or a methyl. The disease or disorder can be diabetes, a cancer, obesity, a neurodegenerative disease, or a combination thereof. The disease or disorder can be a cancer. The cancer can be breast cancer, renal clear cell cancer, bladder cancer, hepatocellular cancer, gastric cancer, cervical cancer, non-small-cell lung cancer, pancreatic cancer, malignant pleural mesothelioma, a colorectal cancer, or a combination thereof.

Also provided herein is the use of a compound that can have a structure according to Formula 1 or pharmaceutical formulation that can include a compound that can have a structure according to Formula 1 for the manufacture of a medicament for treating diabetes, a cancer, obesity, a neurodegenerative disease, or a combination thereof, wherein $R_1$ can be a methyl, an isobutane, a phenyl, an indole, or a butanamine, wherein $R_2$ can be an ethylbenzene, an ethylcyclohexane, an isopentane, a phenyl, a propanamine, or a methylcyclopropane, wherein $R_3$ can be a methylcyclopropane, a propionic acid, an ethylbenzene, or a propanamine, wherein $R_4$ can be a butanamine, a propionic acid, or a phenyl, wherein $R_5$ can be a methylcyclopropane, a propionic acid, or an ethylbenzene, wherein $R_6$ can be a phenyl, a propionic acid, an isobutene, and wherein $R_7$ can be a phenyl, a propionic acid, a butanamine, or a methyl.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
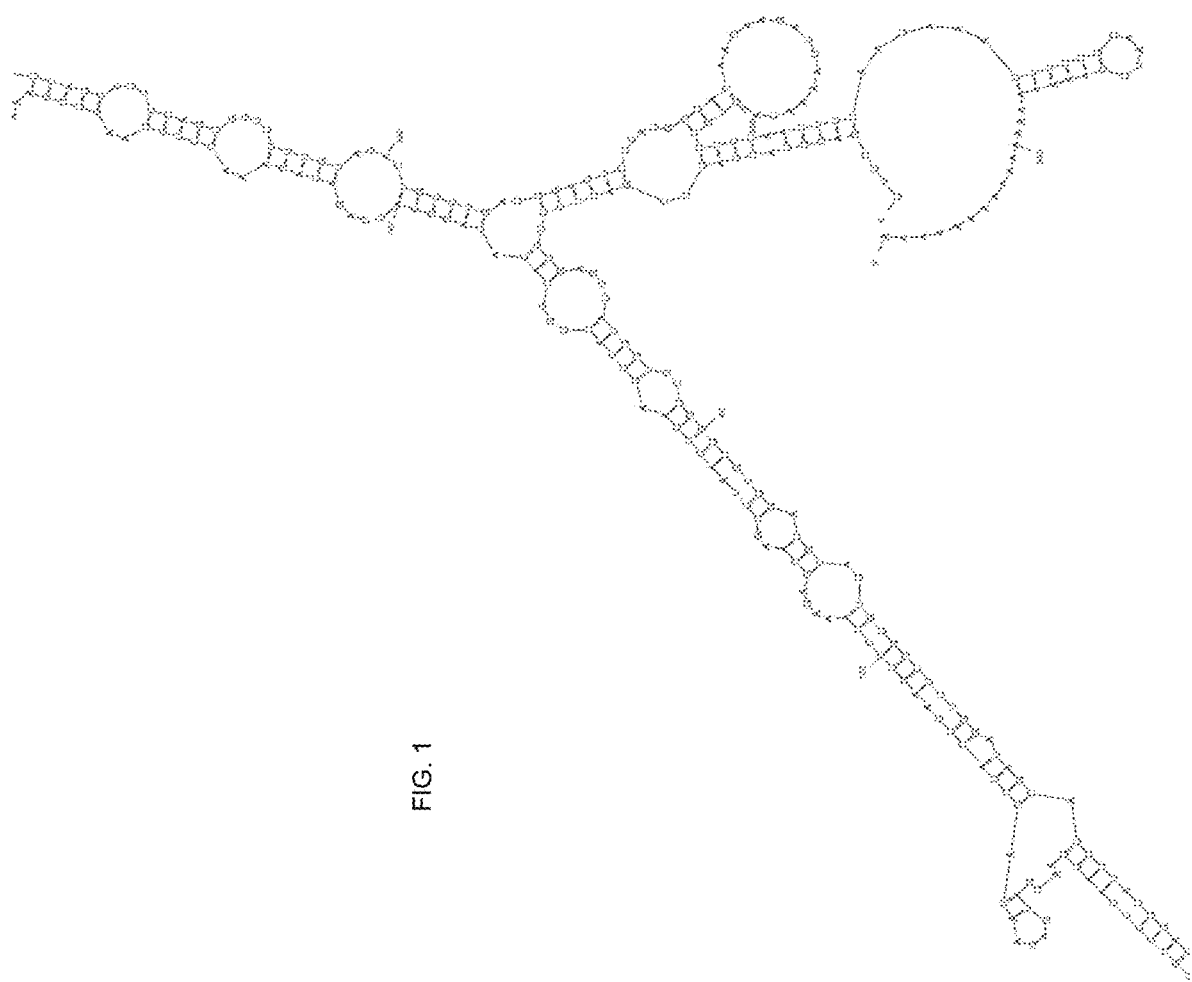
FIG. 1 shows the secondary structure of GAS 5 lncRNA according to SEQ ID NO: 1.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, physiology, biochemistry, botany and the like, which are within the skill of the art. Such techniques are explained fully in the literature.

Definitions

As used herein, "about," "approximately," and the like, when used in connection with a numerical variable, can refer to the value of the variable and to all values of the variable that are within the experimental error (e.g., within the 95% confidence interval for the mean) or within +/−10% of the indicated value, whichever is greater.

As used herein, "additive effect" can refer to an effect arising between two or more molecules, compounds, substances, factors, or compositions that is equal to or the same as the sum of their individual effects.

As used herein, "derivative" can refer to any compound having the same or a similar core structure to the compound but having at least one structural difference, including As used herein, "active derivative" and the like can refer to a modified compound containing a GAS5 binding compound as provided herein. The term "active derivative" and the like can also refer to an analogue provided herein that retains an ability to bind GAS5 lncRNA. Assays for testing the ability of an active derivative to perform in this fashion are known to those of ordinary skill in the art and provided herein. The assays can include, but are not limited to, quantitative real-time PCR, RNA electrophoretic mobility assay, RNA Fluorescence hybridization, western blot analysis, hybrid systems in yeast and mammalian, RNA-immunoprecipitations.

As used herein, "administering" can refer to any administration route, including but not limited to administration that is oral, topical, intravenous, subcutaneous, transcutaneous, transdermal, intramuscular, intra-articular, parenteral, intra-arterial, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, internasal, intrathecal, intrahepatic, intralesional, and intracranial injections or infusion techniques.

As used interchangeably herein, "biocompatible," "biocompatibility," and "biologically compatible" can refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "chemotherapeutic" can refer to a chemical compound or agent used to treat, control, or cure a disease or symptoms thereof, particularly cancer.

As used herein, "composition" or "formulation" can refer to a combination of an active agent(s) and another compound or composition, inert (for example, a detectable agent or label) or active, such as an adjuvant.

As used herein, "a compound of formula (1), (2), (3), (4), (5), (6), (7), (8), (9), (10), (11), (12), (13), (14), and so forth and so on," or "a compound having a structure according to formula (1), (2), (3), (4), (5), (6), (7), (8), (9), (10), (11), (12), (13), (14), etc." can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "control" can refer to an alternative subject or sample used in an experiment for comparison purposes and included to minimize or distinguish the effect of variables other than an independent variable. A control can be positive or negative.

As used herein, "concentrated" can refer to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imines, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with various side groups.

As used herein, "diluted" can refer to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "effective amount" can refer to an amount sufficient to effect beneficial or desired results. An effective amount can be administered in one or more administrations, applications, or dosages. "Effective amount" can refer to an amount of a compound, derivative, and/or formulation thereof provided herein that can treat or prevent diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer. The "effective amount" can also refer to the least amount sufficient to effect beneficial or desired results as described herein.

As used herein, "hydrate" can refer to a compound formed by the addition of water. Typically, but not always, this will be crystalline lattice structures that incorporate water molecules. Hydrates include stoichiometric hydrates, as well as compositions containing variable amounts of water.

As used herein, "mitigate" can refer to reducing a particular characteristic, symptom, or other biological or physiological parameter associated with a disease or disorder.

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein "pharmaceutically effective amount", "effective amount" and the like can refer to an amount of a compound or formulation thereof provided herein that can treat or prevent diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer. In embodiments, the "pharmaceutically effective amount" can be the least amount of a compound or formulation thereof provided herein needed to treat, prevent, or elicit the desired biological and/or medical effect in the response of a cell, tissue, organ, system, or subject that is being sought by the researcher, veterinarian, medical doctor or other clinician. In some embodiments, the "pharmaceutically effective amount" can be the least amount that can treat or prevent diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer "Pharmaceutically effective amount" or "pharmaceutically effective dose," can refer to the amount of a compound or formulation thereof provided herein that will elicit the biological and/or medical response of a cell, tissue, organ, system, or subject that is being sought by the researcher, veterinarian, medical doctor or other clinician. The pharmaceutically effective amount can vary depending on the compound, formulation the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" can refer to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "preventative," "preventing," "prevent" and the like can refer to partially or completely delaying and/or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms including, but not limited to, diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(14) or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "tangible medium of expression" can refer to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "therapeutic", "treating", "treat," and the like can refer to include partially or completely delaying, alleviating, mitigating or reducing the intensity of one or more attendant symptoms of a disease or condition including, but not limited to, diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

As used herein, "C$_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O— alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

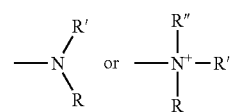

wherein R, R', and R" each independently represent a hydrogen, an alkyl, an alkenyl, —(CH$_2$)$_m$—R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

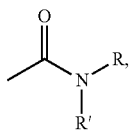

wherein R and R' are as defined above.

As used herein, "Aryl" can refer to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

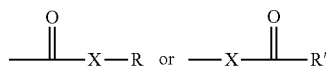

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —$NO_2$; the term "halogen" designates —F, —Cl, —Br, or —I; the term "sulfhydryl" refers to —SH; the term "hydroxyl" refers to —OH; and the term "sulfonyl" refers to —$SO_2$—.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

Discussion

Diabetes mellitus (DM) is a complex and costly disease that is increasing in prevalence worldwide. In 2012, it was estimated that diabetes costs the nation $245 billion, a 41% increase from costs incurred in 2007 (ADA study "Economic Costs of Diabetes in the US in 2012"). According to the American Diabetes Association (ADA), about 9.3% of the United States population is diagnosed with diabetes. Diabetes remains the seventh leading cause of death in the United States and caused about 69,000 deaths in 2010. Diabetes was listed as a contributing factor or underlying cause of an additional 234,000 deaths in 2010. Further, it is estimated that 79 million in the United States have pre-diabetes and 1 in 4 have an un-diagnosed state of diabetes.

Recently, it has been reported that the long non-coding RNA (lncRNA) GAS5 were reduced in serum from diabetic patients. Further in vitro knockdown of GAS5 in lean adipocytes demonstrated a marked decrease in PPARA expression. Dysregulation or aberrant expression of GAS5 has been reported in other diseases as well, such as cancer (including but not limited to gastric cancer and prostate cancer, diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

With that said, described herein are compounds that can bind the GAS5 lncRNA, formulations thereof, and uses thereof. The compounds can be capable of modulating the interaction of GAS5 RNA with other enzymes and compounds such that the amount and/or the activity of the GAS5 lncRNA is altered from its normal or a baseline state. The compounds and formulations thereof provided herein can be administered to a subject in need thereof. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

GAS 5 Binding Compounds and Compositions

GAS5 is a lncRNA having about 651 bp and can have a cDNA sequence that can be 90%-100% identical with SEQ ID NO: 1. FIG. 1 shows the secondary structure of a GAS 5 lncRNA according to SEQ ID NO: 1. Turnover of GAS5 can be mediated by enzymes that bind to and otherwise interact with the GAS5 lncRNA. One example of such an enzyme is UPF1, which is involved in mediating nonsense mediated RNA decay. The GAS5 lncRNA has a premature termination codon, which can render the GAS5 lncRNA more susceptible to nonsense mediated RNA decay. It has been demonstrated that when UPF1 is depleted that levels of GAS5 lncRNA increase. Additionally, it has been observed that adipocytes from subjects with DM have increased amounts of UPF1 and concurrent decreased amounts of GAS5 lncRNA as compared to non-DM adipocytes.

Provided herein are compounds that can bind GAS5 lncRNA. In some embodiments, the compounds can specifically bind GAS5 lncRNA. The compounds described herein can directly bind (i.e. not via an intermediate molecule) GAS5 lncRNA. In some embodiments, the compounds that can bind GAS5 lncRNA can de-stabilize and/or inhibit binding of an enzyme to the GAS5 lncRNA. In other embodiments, the compounds that can bind GAS5 lncRNA can stabilize, stimulate, and/or facilitate binding of an enzyme to the GAS5 lncRNA. Binding of the GAS5 lncRNA by the compounds provided herein can be capable of altering the half-life of the GAS5 lncRNA and/or total amount of GAS lnRNA present in a cell and/or subject.

In some embodiments, when the compound that can bind the GAS5 lncRNA de-stabilizes and/or inhibits binding of an enzyme to the GAS5 lncRNA binds the GAS5 mRNA the GAS5 mRNA is not degraded and/or its activity is not interrupted. In some of these embodiments, the overall amount of GAS5 lncRNA can be increased as compared to amount present prior to the exposure of the GAS5 lncRNa to a GAS5 binding compound provided herein. In some embodiments, when the compound that can bind the GAS5 lncRNA stabilizes, stimulates, and/or facilitates binding of an enzyme to the GAS5 lncRNA binds the GAS5 lncRNA the GAS5 lncRNA can be degraded and/or the activity of the GAS5 lncRNA can be inhibited. In some of these embodiments, the overall amount of GAS5 lncRNA can be decreased as compared to the amount of GAS5 lncRNA present prior to exposure of the GAS5 lncRNA to a GAS5 binding compound provided herein.

The compound can have a structure according to Formula 1 or be a derivative thereof,

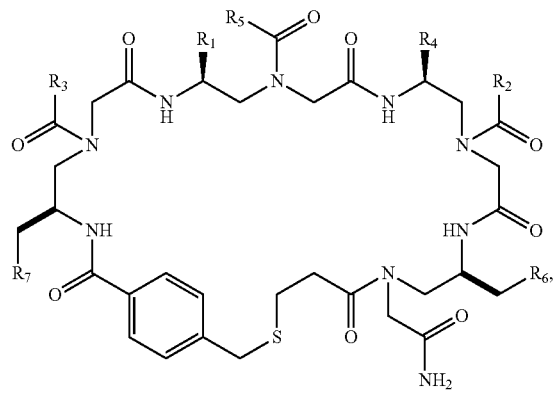

Formula 1 wherein $R_1$ is a methyl, an isobutane, a phenyl, an indole, or a butanamine, wherein $R_2$ is an ethylbenzene, an ethylcyclohexane, an isopentane, a phenyl, a propanamine, or a methylcyclopropane, wherein $R_3$ is a methylcyclopropane, a propionic acid, an ethylbenzene, or a propanamine wherein $R_4$ is a butanamine, a propionic acid, or a phenyl, wherein $R_5$ is a methylcyclopropane, a propionic acid, or an ethylbenzene, wherein $R_6$ is a phenyl, a propionic acid, an isobutene, and wherein $R_7$ is a phenyl, a propionic acid, a butanamine, or a methyl. In some embodiments, the compound can have a structure according to any one of Formulas 3-19:

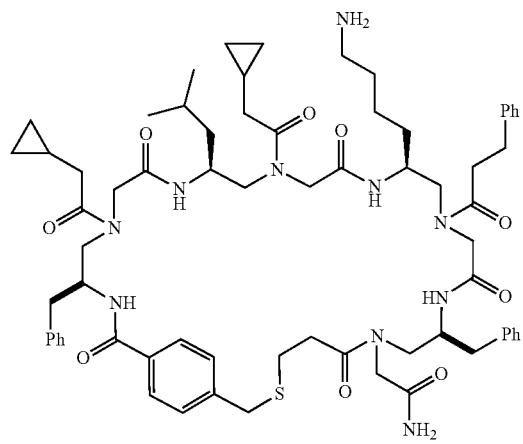

Formula 3

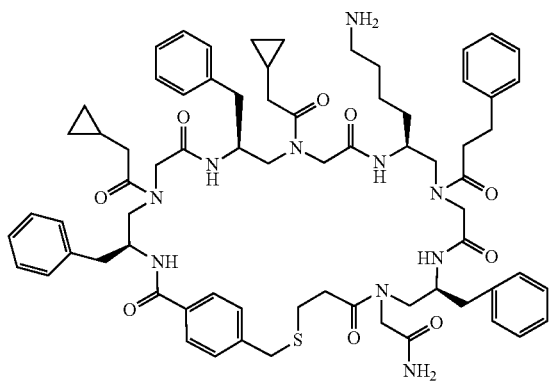

Formula 4

-continued
Formula 5
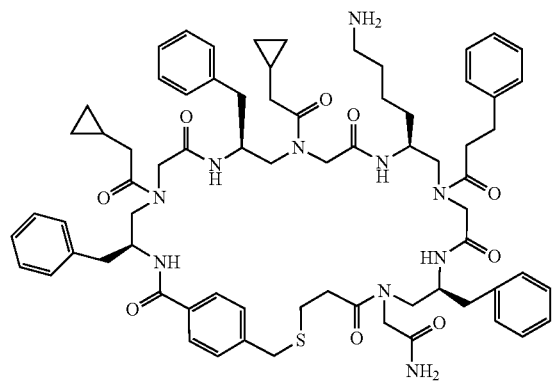
Formula 6
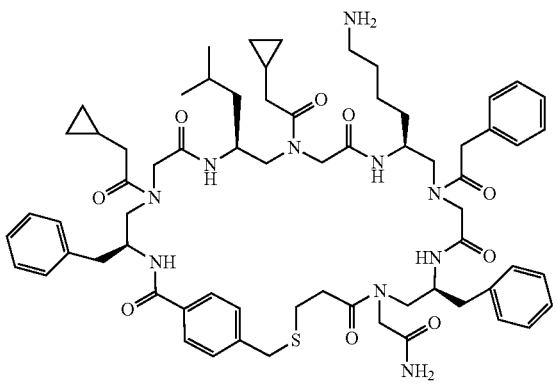
Formula 7
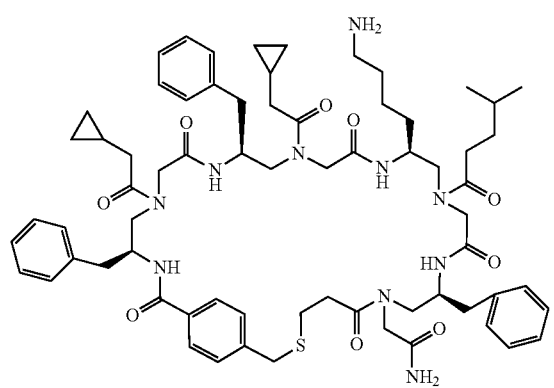
Formula 8
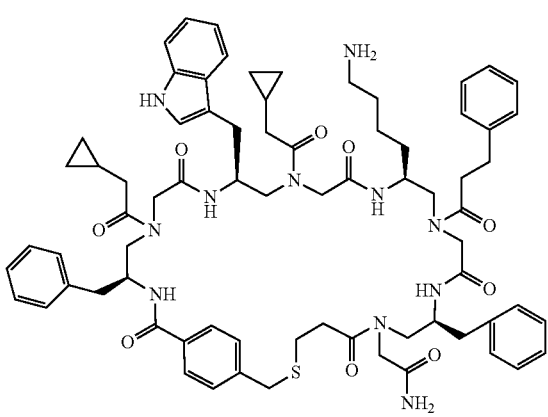
Formula 9
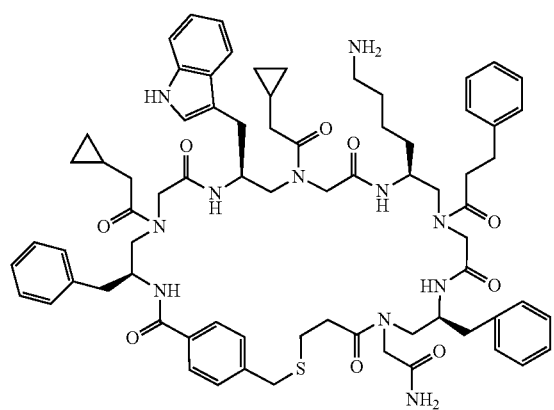
Formula 10
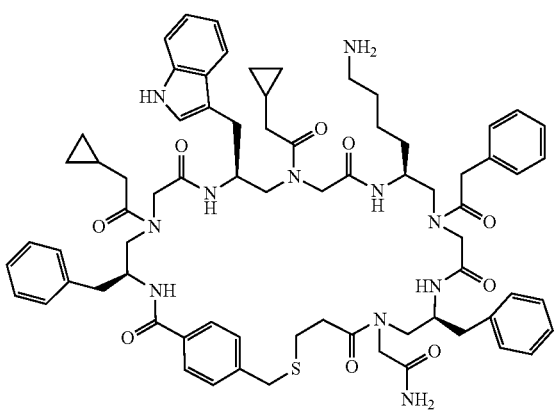

Formula 11
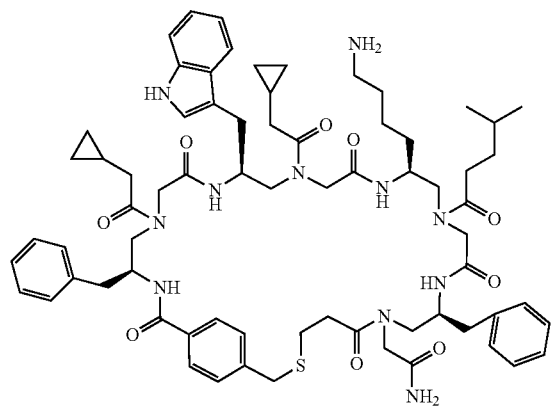
Formula 12
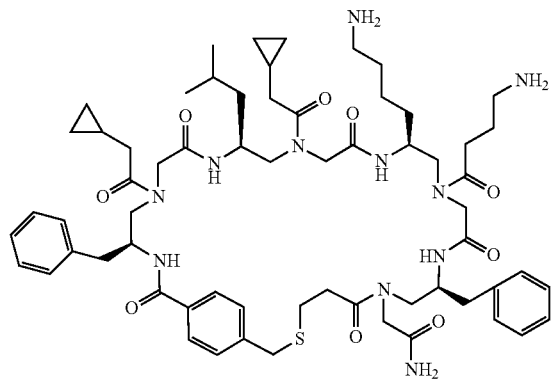
Formula 13
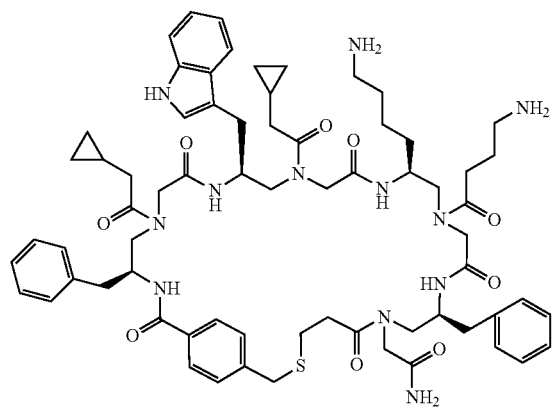
Formula 14
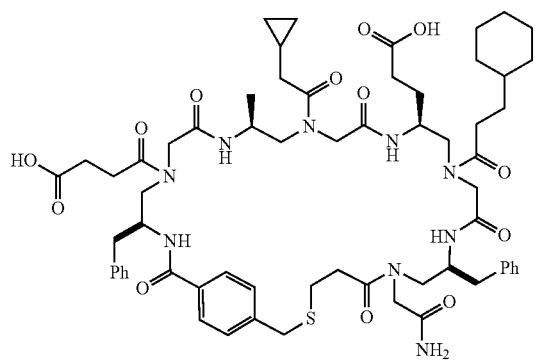
Formula 15
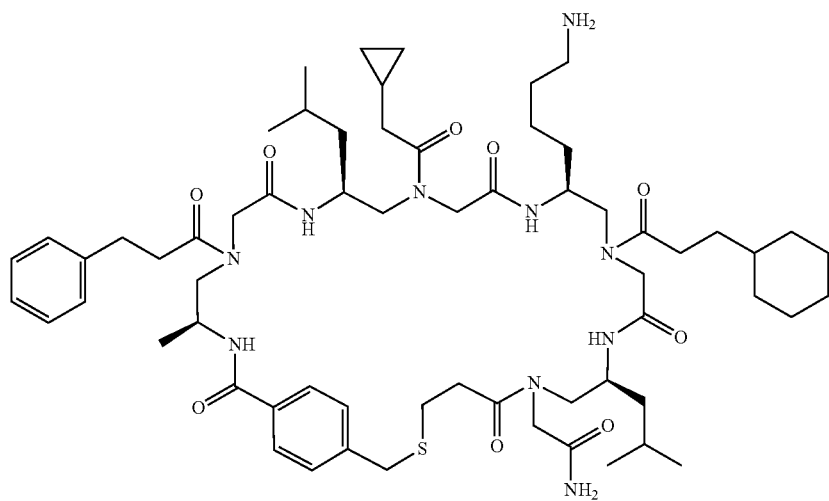

Formula 16

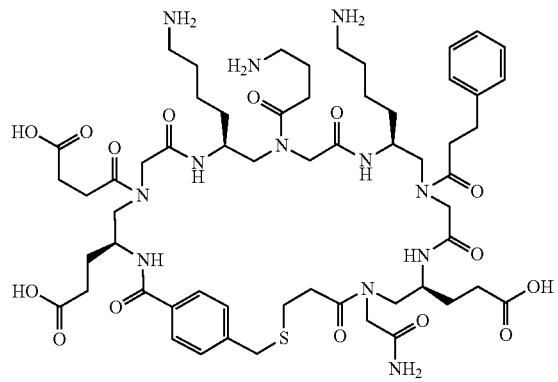

Formula 17

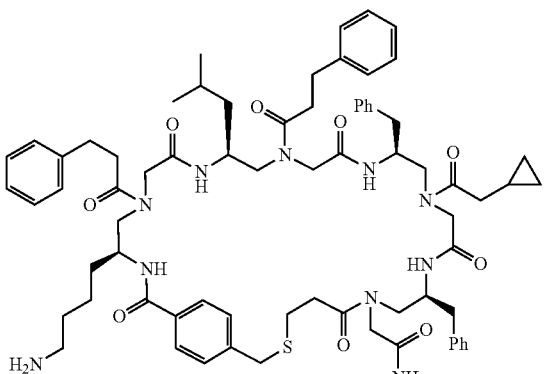

Formula 18

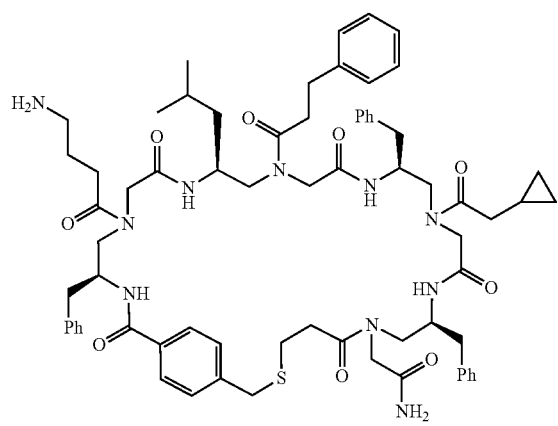

Formula 19

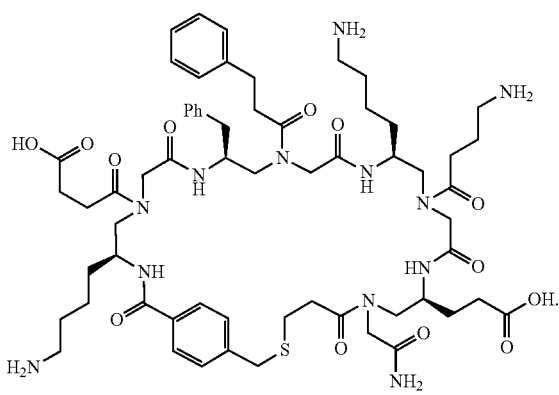

Any compound with a structure according to Formula 1 and any derivative thereof can be substituted with a suitable substituent.

In some embodiments, the compound can have a structure according to Formula 2 or be a derivative thereof, Formula 2

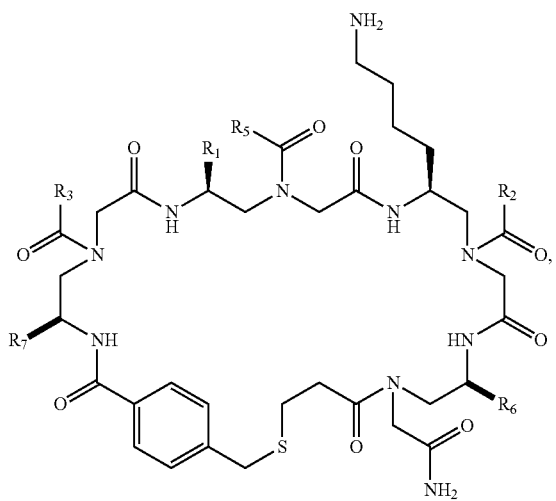

wherein $R_1$ is an isobutane, a phenyl, an indole, or a butanamine, wherein $R_2$ is an ethylbenzene, an ethylcyclohexane, an isopentane, a phenyl, or a propanamine, wherein $R_3$ is a methylcyclopropane, a propionic acid, or an ethylbenzene, wherein $R_5$ is a methylcyclopropane, a propan- amine, or an ethylbenzene, wherein $R_6$ is a phenyl, a propionic acid, an isobutene, and wherein $R_7$ is a phenyl, a propionic acid, a butanamine, or a methyl. In some embodiments the compound with a structure according to Formula 2 can have a structure according to any one of Formulas 3, 4, 5, 6, 7, 8, 9, 10, 11, 12, 13, 15, 16, or 19. Any compound with a structure according to Formula 2 and any derivative thereof can be substituted with a suitable substituent.

In some embodiments, the compound can have a structure according to Formula 20 or be a derivative thereof, Formula 20

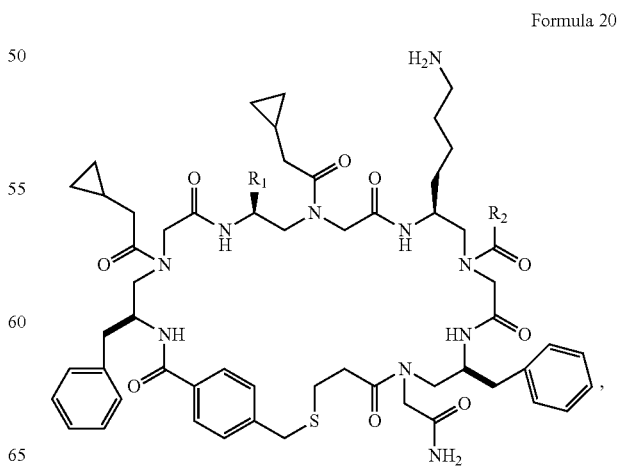

wherein $R_1$ is an isobutene, a phenyl, or an indole and wherein $R_2$ is an ethylbenzene, a phenyl, an isobutene, or a propanamine. In some embodiments the compound with a structure according to Formula 20 can have a structure according to any one of Formulas 3, 4, 5, 6, 7, 8, 9, 10, 11, 12, or 13. Any compound with a structure according to Formula 20 and any derivative thereof can be substituted with a suitable substituent.

In some embodiments, the compound can have a structure according to Formula 21 or be a derivative thereof Formula 21

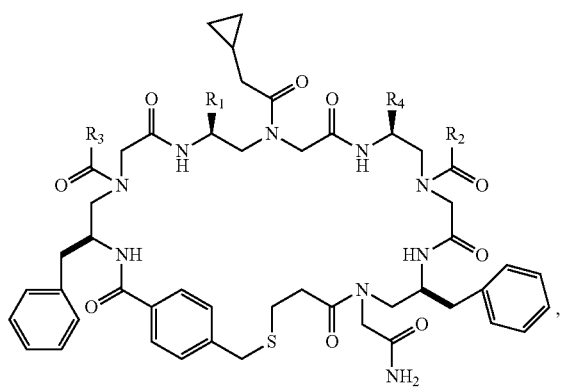

wherein $R_1$ is an isobutene, a phenyl, an indole, or a methyl, wherein $R_2$ is an ethylbenzene, a phenyl, an isobutene, a propanamine, or an ethylcyclohexane, wherein $R_3$ is a methylcyclopropane or a propionic acid, and wherein $R_4$ is a butanamine or a propionic acid. In some embodiments the compound with a structure according to Formula 21 can have a structure according to any one of Formulas 3, 4, 5, 6, 7, 8, 9, 10, 11, 12, 13, or 14. Any compound with a structure according to Formula 21 and any derivative thereof can be substituted with a suitable substituent.

In some embodiments, the compound can have a structure according to Formula 22 or be a derivative thereof Formula 22

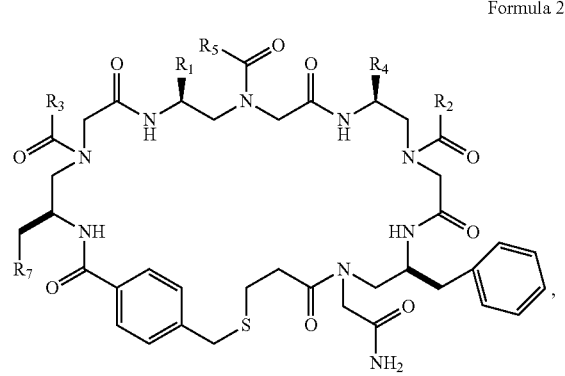

wherein $R_1$ is an isobutene, a phenyl, an indole, or a methyl, wherein $R_2$ is an ethylbenzene, a phenyl, an isobutene, a propanamine, an ethylcyclohexane, or a methylcyclopropane, wherein $R_3$ is a methylcyclopropane, propionic acid, ethylbenzene, or a propanamine, wherein $R_4$, is a butanamine or a propionic acid, and wherein $R_5$ is a methylcyclopropane and ethylbenzene. In some embodiments the compound with a structure according to Formula 22 can have a structure according to any one of Formulas 3, 4, 5, 6, 7, 8, 9, 10, 11, 12, 13, 14, 17, or 18. Any compound with a structure according to Formula 22 and any derivative thereof can be substituted with a suitable substituent.

In some embodiments, the compound can have a structure according to Formula 22 or be a derivative thereof Formula 23

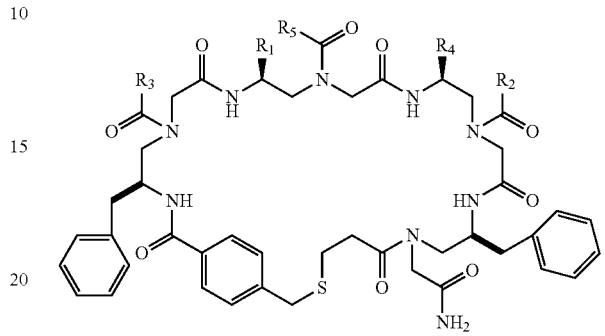

wherein $R_1$ is an isobutene, a phenyl, an indole, or a methyl, wherein $R_2$ is an ethylbenzene, a phenyl, an isobutene, a propanamine, or an ethylcyclohexane, wherein $R_3$ is a methylcyclopropane or a propanamine, wherein $R_4$ is a butanamine or a propionic acid, and wherein $R_5$ is a methyl cyclopropane or an ethylbenzene. In some embodiments the compound with a structure according to Formula 23 can have a structure according to any one of Formulas 3, 4, 5, 6, 7, 8, 9, 10, 11, 12, 13, 14, or 18. Any compound with a structure according to Formula 23 and any derivative thereof can be substituted with a suitable substituent.

Pharmaceutical Formulations

The compounds (e.g. compounds having a structure according to any one of formulas 1-19 and derivatives thereof) described herein can be provided to a subject in need thereof as an ingredient, such as an active ingredient, in a pharmaceutical formulation. As such, also described are pharmaceutical formulations containing one or more of the compounds and salts thereof, or pharmaceutically acceptable salts thereof described herein. Suitable salts include, but are not limited to, sulfate, citrate, acetate, oxalate, chloride, hydrochloride, bromide, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

The pharmaceutical formulations or salts thereof can be administered to a subject in need thereof. In some embodiments, the subject has diabetes, cancer Obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer. In embodiments, the compounds described herein are used in the manufacture of a medicament for the treatment of diabetes, a cancer, Obesity, neurodegenerative diseases, breast cancer, renal clear cell cancer, bladder cancer, hepatocellular cancer, gastric cancer, cervical cancer, non-smallcell lung cancer, pancreatic cancer, malignant pleural mesothelioma, and/or colorectal cancer.

Pharmaceutically Acceptable Carriers and Auxiliary Ingredients and Agents

The pharmaceutical formulations containing an effective amount of a compound described herein (e.g. compounds having a structure according to any one of formulas 1-19) or a derivative thereof can further include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In addition to the effective amount of a compound and/or derivative thereof, the pharmaceutical formulations can also include an effective amount of auxiliary active agents, including but not limited to, antisense or RNA interference molecules, chemotherapeutics, or antineoplasic agents, hormones, antibiotics, antivirals, immunomodulating agents, antinausea, pain modifying compounds (such as opiates), anti-inflammatory agents, antipyretics, antibiotics, and/or antibodies or fragments thereof.

Effective Amounts of the Compounds, Derivatives Thereof, and Auxiliary Active Agents The effective amount of the compound ((e.g. compounds having a structure according to any one of formulas 1-19), or derivative thereof contained in the pharmaceutical formulation can range from about 0.001 micrograms to about 1000 grams. In some embodiments, the effective amount of the compound and/or derivative thereof can range from about 0.001 micrograms to about 0.01 micrograms. In other embodiments, the effective amount of compound and/or derivative thereof can range from about 0.01 micrograms to about 0.1 micrograms. In further embodiments, the effective amount of the compound and/or derivative thereof can range from about 0.1 micrograms to about 1.0 grams. In yet further embodiments, the effective amount of the compound and/or derivative thereof can range from about 1.0 grams to about 10 grams. In other embodiments, the effective amount of the compound and/or derivative thereof can range from about 10 grams to about 100 grams. In still other embodiments, the effective amount of the compound and/or derivative thereof can range from about 100 grams to about 1000 grams.

In embodiments where there is an auxiliary active agent contained in the compound or derivative thereof pharmaceutical formulation, the effective amount of the auxiliary active agent will vary depending on the auxiliary active agent. In some embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total pharmaceutical formulation.

The auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In embodiments where the auxiliary active agent is a stand-alone compound or pharmaceutical formulation, the effective amount of the auxiliary active agent can vary depending on the auxiliary active agent used. In some of these embodiments, the effective amount of the auxiliary active agent can range from 0.001 micrograms to about 1000 grams. In other embodiments, the effective amount of the auxiliary active agent can range from about 0.01 IU to about 1000 IU. In further embodiments, the effective amount of the auxiliary active agent can range from 0.001 mL to about 1000 mL. In yet other embodiments, the effective amount of the auxiliary active agent can range from about 1% w/w to about 50% w/w of the total auxiliary active agent pharmaceutical formulation. In additional embodiments, the effective amount of the auxiliary active agent can range from about 1% v/v to about 50% v/v of the total pharmaceutical formulation. In still other embodiments, the effective amount of the auxiliary active agent can range from about 1% w/v to about 50% w/v of the total auxiliary agent pharmaceutical formulation.

Dosage Forms

In some embodiments, the pharmaceutical formulations described herein can be in a dosage form. The dosage form can be administered to a subject in need thereof. In some embodiments, the subject in need thereof can have cancer, obesity, diabetes, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. In some embodiments, this is a subject having diabetes, obesity, cancer, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

Where appropriate, the dosage forms described herein can be microencapsulated.

The dosage form can also be prepared to prolong or sustain the release of any ingredient. In some embodiments, the compound or derivative thereof is the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, compound, derivative thereof, auxiliary active ingredient, and/or pharmaceutically acceptable salt thereof are incorporated into a liposome. In some embodiments, a compound, derivative thereof, auxiliary active ingredient, and/or pharmaceutically acceptable salts thereof is integrated into the lipid membrane of the liposome. In other embodiments, a compound, derivative thereof, auxiliary active ingredient, and/or pharmaceutically acceptable salt thereof are contained in the aqueous phase of the liposome. In embodiments where the dosage form is a liposome, the pharmaceutical formulation is thus a liposomal formulation. The liposomal formulation can be administered to a subject in need thereof. In some embodiments, this is a subject having diabetes, obesity, cancer, diabetes, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the compound, derivative thereof, auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the compound, derivative thereof, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators. The nasal/inhalation formulations can be administered to a subject in need thereof. In some embodiments, this is a subject having diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

In some embodiments, the dosage forms are aerosol formulations suitable for administration by inhalation. In some of these embodiments, the aerosol formulation contains a solution or fine suspension of a compound, derivative thereof, auxiliary active ingredient, and/or pharmaceutically acceptable salt thereof a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a compound, derivative thereof, auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof. In some embodiments, this can be a subject having diabetes, obesity, cancer, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

For some dosage forms suitable and/or adapted for inhaled administration, the pharmaceutical formulation is a dry powder inhalable formulations. In addition to the compound, derivative thereof, auxiliary active ingredient, and/or pharmaceutically acceptable salt thereof, such a dosage form can contain a powder base such as lactose, glucose, trehalose, manitol, and/or starch. In some of these embodiments, the compound, derivative thereof, auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the compounds described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof. In some embodiments, this is a subject having diabetes or a cancer, obesity, diabetes, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

Dosage forms adapted for parenteral administration and/or adapted for injection can include aqueous and/or non-aqueous sterile injection solutions, which can contain antioxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof. In some embodiments, this can be a subject having cancer, obesity, diabetes, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

For some embodiments, the dosage form contains a predetermined amount of a compound and/or derivative thereof per unit dose. In an embodiment, the predetermined amount of the compound or derivative thereof is an effective amount of the compound and/or derivative thereof to treat, prevent, or mitigate one or more symptoms of diabetes, cancer, obesity, diabetes, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer. In other embodiments, the predetermined amount of the compound and/or derivative thereof can be an appropriate fraction of the effective amount of the active ingredient. Such unit doses may therefore be administered once or more than once a day (e.g. 1, 2, 3, 4, 5, 6, or more times per day). Such pharmaceutical formulations may be prepared by any of the methods well known in the art.

Methods of Making the Compounds and Derivatives Thereof

The compounds (e.g. compounds having a structure according to any one of formulas 1-19) and derivatives thereof can be synthesized via many methods generally known to those of ordinary skill in the art. The present disclosure is not intended to be limited by the particular methods of synthesizing the compounds described herein. The skilled artisan will recognize additional methods of synthesizing the compounds described herein.

Methods of Use

Any amount of the compounds (e.g. compounds having a structure according to any one of formulas 1-19) or derivatives thereof, pharmaceutical formulations, and/or salts thereof described herein can be administered to a subject in need thereof one or more times per day, week, month, or year. In some embodiments, the amount administered is the effective amount of the compound, derivative thereof, pharmaceutical formulation, and/or salt thereof. For example, the compounds, formulations, or salts thereof, can be administered in a daily dose. This amount may be given in a single dose per day. In other embodiments, the daily dose may be administered over multiple doses per day, in which each containing a fraction of the total daily dose to be administered (sub-doses). In some embodiments, the amount of doses delivered per day is 2, 3, 4, 5, or 6. In further embodiments, the compounds, formulations, or salts thereof are administered one or more times per week, such as 1, 2, 3, 4, 5, or 6 times per week. In other embodiments, the compounds, formulations, or salts thereof are administered one or more times per month, such as 1 to 5 times per month. In still further embodiments, the compounds, formulations, or salts thereof are administered one or more times per year, such as 1 to 11 times per year.

In some embodiments, the subject in need thereof is a subject having diabetes, cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, colorectal cancer.

In embodiments where more than one of compounds, formulations, additional therapeutic agents, salts thereof, or pharmaceutically acceptable salts thereof are administered to a subject in need thereof sequentially; the sequential administration may be close in time or remote in time. For example, administration of the second compound, formulation, or other therapeutic agent can occur within seconds or minutes (up to about 1 hour) after administration of the first agent (close in time). In other embodiments, administration of the second compound, formulation, or other therapeutic agent occurs at some other time that is more than an hour after administration of the first agent.

The amount of compounds, formulations, salts thereof (including pharmaceutically acceptable formulations and salts thereof) described herein can be administered in an amount ranging from about 0.01 mg to about 1000 mg per day, as calculated as the free or unsalted compound.

The compounds and formulations described herein can be administered in combinations with or include one or more other auxiliary agents. Suitable auxiliary agents include, but are not limited to antisense or RNA interference molecules, chemotherapeutics, anti-neoplasic agents, hormones, antibiotics, antivirals, immunomodulating agents, anti-nausea, pain modifying compounds (such as opiates), anti-inflammatory agents, antipyretics, antibiotics, and/or antibodies or fragments thereof. The compound(s), and/or formulation(s), and/or additional therapeutic agent(s) can be administered simultaneously or sequentially by any convenient route in separate or combined pharmaceutical formulations. The additional therapeutic agents can be provided in their optically pure form or a pharmaceutically acceptable salt thereof.

Kits

The compounds (e.g. compounds having a structure according to any one of formulas 1-19, including derivatives thereof) and pharmaceutical formulations described herein can be presented as a combination kit. As used herein, the terms "combination kit" or "kit of parts" refers to the compounds, or pharmaceutical formulations and additional components that are used to package, sell, market, deliver, and/or administer the combination of elements or a single element, such as the active ingredient, contained therein. Such additional components include but are not limited to, packaging, syringes, blister packages, bottles, and the like. When one or more of the components (e.g. active agents) contained in the kit are administered simultaneously, the combination kit can contain the active agents in a single pharmaceutical formulation (e.g. a tablet) or in separate pharmaceutical formulations.

When the agents are not administered simultaneously, the combination kit can contain each agent in separate pharmaceutical formulations. The separate pharmaceutical formulations can be contained in a single package or in separate packages within the kit.

In some embodiments, the combination kit also includes instructions printed on or otherwise contained in a tangible medium of expression. The instructions can provide information regarding the content of the compound or pharmaceutical formulations contained therein, safety information regarding the content of the compound(s) or pharmaceutical formulation(s) contained therein, information regarding the dosages, indications for use, and/or recommended treatment regimen(s) for the compound(s) and/or pharmaceutical formulations contained therein. In some embodiments, the instructions provide directions for administering the compounds, pharmaceutical formulations, or salts thereof to a subject having diabetes, a cancer, obesity, neurodegenerative diseases, breast cancer, renal clear cell cancer, bladder cancer, hepatocellular cancer, gastric cancer, cervical cancer, non-small-cell lung cancer, pancreatic cancer, malignant pleural mesothelioma, and/or colorectal cancer.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

RNA folds and has secondary structures. Usually the stem-loop structures recruit & bind to proteins. The TAA is part of stem-loop structure that can be involved in recruiting proteins and allow for nonsense mediated decay. This Example can at least demonstrate the design of a compound that can bind to this region and block its turnover. This can increase GAS5 levels in diseases such as diabetes.

Figure 3A:
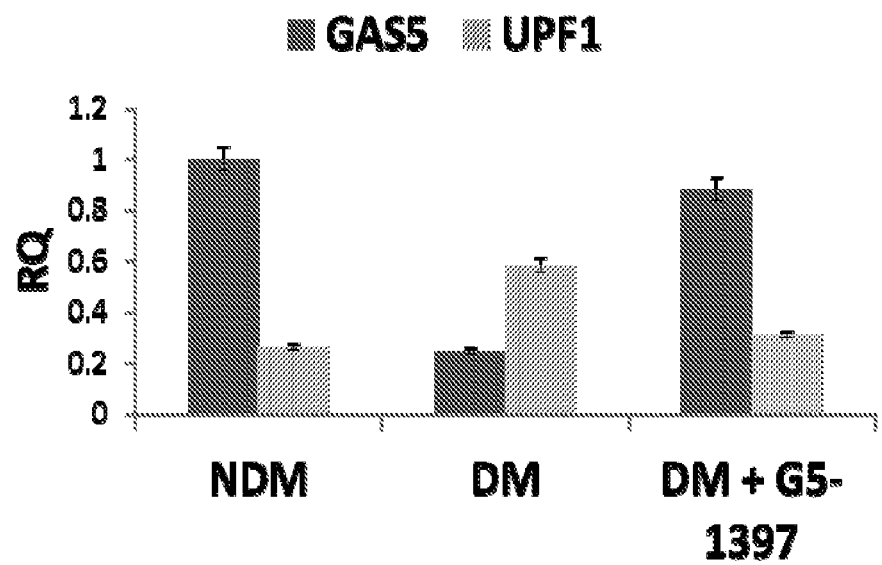
FIGS. 3A and 3B show graphs demonstrating the results from a qPCR of GAS5 and UPF1 (n=4) (FIG. 3A) and results from a cell viability assay after treatment with compound G5-1397 (FIG. 3B).

Strategy for compound design: GAS5 transcript may be targeted to faster turnover by nonsense mediated RNA decay. GAS5 transcript has a premature termination codon which renders greater susceptibility for nonsense mediated RNA decay. It was demonstrated that GAS5 levels were increased when UPF1, an essential component of nonsense mediated RNA decay, was depleted (Tani, H., Torimura, M., and Akimitsu, N. (2013) The RNA degradation pathway regulates the function of GAS5 a non-coding RNA in mammalian cells. *PloS One* 2013; 8(1):e55684. doi: 10.1371/journal.pone.0055684). This demonstrated an inverse relationship of UPF1 and GAS5. Amongst known UPF1 targets are genes associated with diabetes (COIL, ITPR3, TRIM32) which were upregulated when UPF1 was depleted (Tani, H., Imamachi, N., Salam, K. A., Mizutani, R., Ijiri, K., Irie, T., Yada, T., Suzuki, Y., and Akimitsu, N. (2012) Identification of hundreds of novel UPF1 target transcripts by direct determination of whole transcriptome stability. *RNA biology* 9, 1370-1379). GAS5 and UPF1 levels were measured in NDM and DM adipocytes. The data indicated that GAS5 levels were low in DM adipocytes concurrent with increased expression of UPF1 compared to NDM adipocytes (FIG. 3A).

The results using AHD-058-6 showed that inhibiting UPF1 in DM increased GAS5 levels (not shown due to page constraints). However, it is not advisable to inhibit UPF1 since it is integral to nonsense mediated decay, which is an important surveillance mechanism to reduce errors in gene expression. Additionally in humans, UPF1 is used for S phase progression and genome stability (Azzalin C M, Lingner J. The human RNA surveillance factor UPF1 is important for S phase progression and genome stability. Curr Biol. 2006; 16(4):433-9. doi: 10.1016/j.cub.2006.01.018. PubMed PMID: 16488880 and Azzalin C M. UPF1: a leader at the end of chromosomes. Nucleus. 2012; 3(1):16-21. PubMed PMID: 22156744.) A strategy was designed to disrupt the binding of UPF1 to GAS5 thereby inhibiting GAS5 turnover. GAS5 has premature stop codons UAA upstream of the poly(A) tail. UPF1 binds to this region and tags it for nonsense mediated decay (Tani H, Torimura M, Akimitsu N. The RNA degradation pathway regulates the function of GAS5 a non-coding RNA in mammalian cells. PloS one. 2013; 8(1):e55684. Epub 2013/02/06. doi: 10.1371/journal.pone.0055684. PubMed PMID: 23383264; PubMed Central PMCID: PMC3559549).

Figure 2:
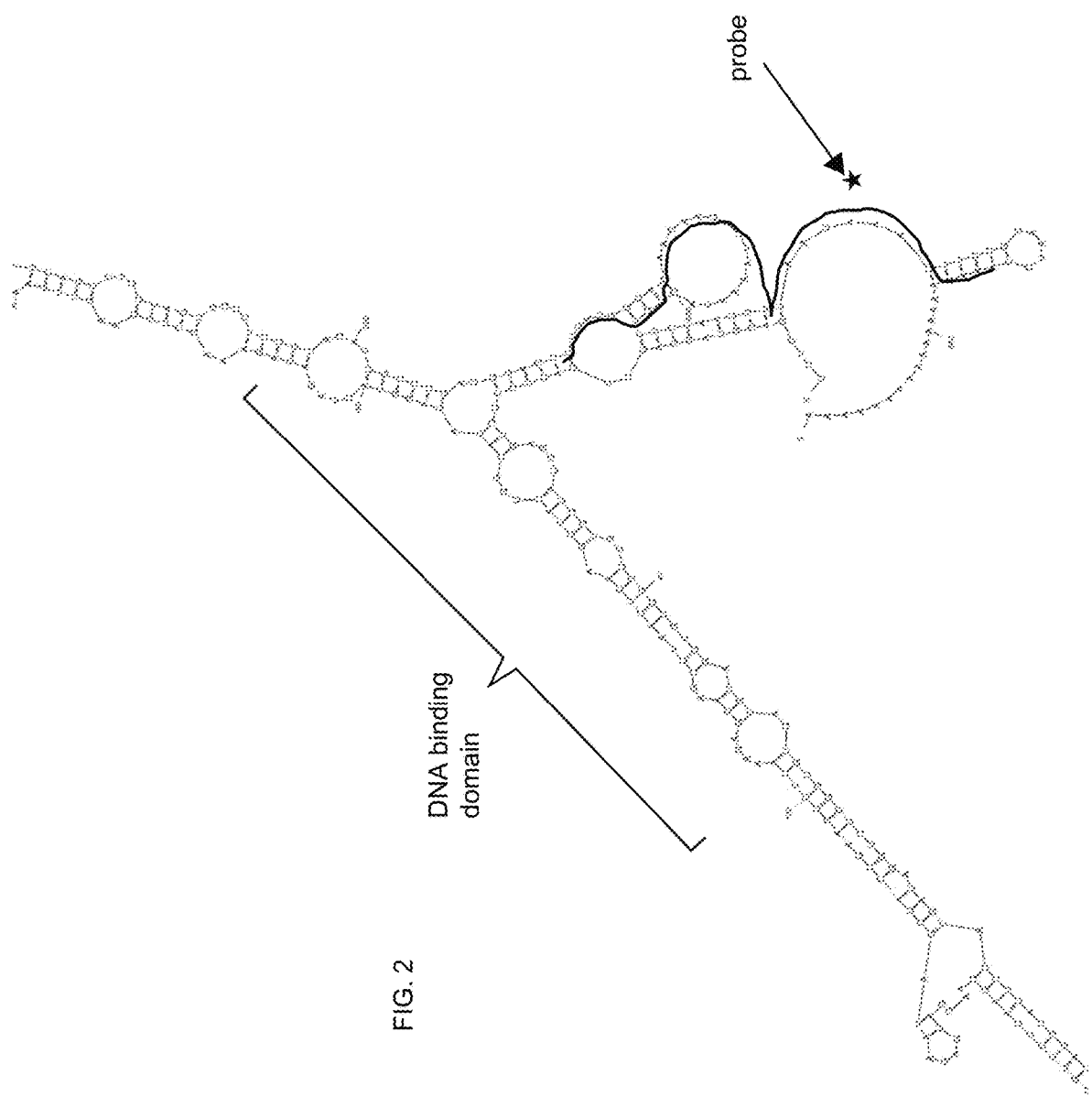
FIG. 2 shows the secondary structure of GAS 5 lncRNA and relevant protein and DNA binding site(s) and binding of a GAS5 lncRNA fluorescently labeled probe.

The interaction between UPF1 and GAS5 was disrupted using a γ-AApeptide based one-bead-one-compound (OBOC) combinatorial library (Wu H, Li Y, Bai G, Niu Y, Qiao Q, Tipton J D, Cao C, Cai J. gamma-AApeptide-based small-molecule ligands that inhibit Abeta aggregation. Chemical communications. 2014; 50(40):5206-8. doi: 10.1039/c3cc46685j. PubMed PMID: 24158240). The γ-AApeptide is a peptidomimetic with side chains for chemical diversity and are resistant to proteolytic cleavage. To screen the compound library, a probe that contained a fluorescein tagged oligonucleotide was synthesized. The probe spanned 30 nucleotides on either side of the UAA sequences on GAS5 (FIG. 2) The fluorescein was attached to the 5'end (beginning of oligonucleotide probe sequence). The nucleotide sequence within the GAS5 lncRNA that the oligonucleotide probe binds to can be about 100% identical to CTCCCAGTGGTCTTTGTAGACTGCCTGATGGAG-TCTCATGGCACAAGAAGAT<u>TAA</u>AACA GTGTCTCC- AATTTTAATAAATTTTTGCAATCCAAAAAAAAAAAAAAAAAAAAA (SEQ ID NO: 2), which is nucleotides 541 to 651 of SEQ ID NO: 1. The underlined regions indicate the UAA that is the target regions. As such, the oligonucleotide probe was designed to flank both sides of these target regions.

This is at the 3' end of the transcript (near poly(A) tail) and does not interfere with 5' DNA binding domain of GAS5, which interacts with the insulin receptor. The length of oligonucleotide was required to maintain stem loop structure to specifically bind to GAS5. Further, we modeled the oligonucleotide (RNAfold software) to evaluate its folding and verified absence of any unwanted secondary structures. The backbone was modified by 2'-MOE (2'-O-methoxyethylribose), which protects it from degradation and a fluroscein tag was attached to the 5'end to aid in screening. The oligonucleotide probe was used to screen 160,000 molecules in the combinatorial library using tRNA as control (as tRNA has similar stem loop secondary structures). Four positive beads were identified which demonstrated the stringent conditions and high specificity of binding. These compounds were tested in vitro for their ability to disrupt binding of UPF1 to GAS5 thereby protecting it from turnover via nonsense mediated decay. Compounds have a structure according to Formulas 3 (also referred to herein as G5-1397), derivatives thereof and Formula 14 were identified and validated as being able to bind GAS5. The compound having a structure according to Formula 3 was determined to have a chemical formula of $C_{68}H_{92}N_{10}O_9S$, a mass of about 1224.6769, and a molecular weight of 1225.6050. The compound having a structure according to Formula 14 was determined to have a chemical formula of $C_{63}H_{85}N_9O_{13}S$, a mass of about 1207.5988, and a molecular weight of 1208.4830.

Figure 3B:
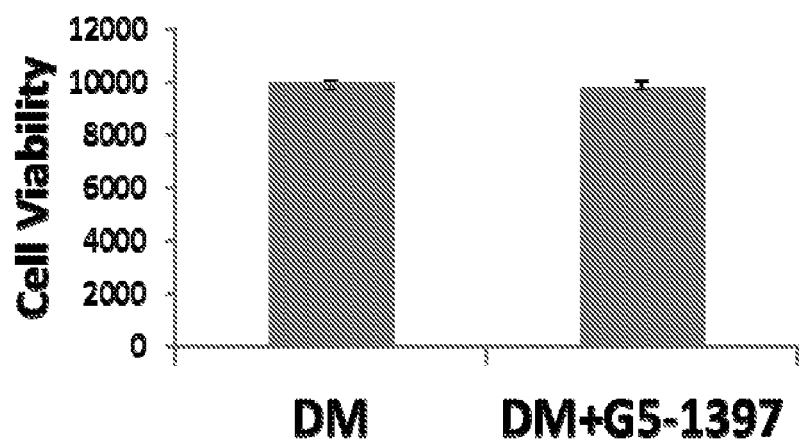

DM adipocytes were treated with G5-1397 (20 nM) for about 24 hours. GAS5 levels were measured using SYBR Green qPCR. The results show G5-1397 substantially increases GAS5 levels in DM adipocytes (FIGS. 3A-3B). Further, G5-1397 increased GAS5 without causing cell toxicity.

RNA-EMSA was performed as previously described (see e.g. Apostolatos, H., Apostolatos, A., Vickers, T., Watson, J. E., Song, S., Vale, F., Cooper, D. R., Sanchez-Ramos, J., and Patel, N. A. (2010) Vitamin A metabolite, all-trans-retinoic acid, mediates alternative splicing of protein kinase C deltaVIII (PKCdeltaVIII) isoform via splicing factor SC35. *J Biol Chem* 285, 25987-25995 and Patel, R. S., Carter, G., Cooper, D. R., Apostolatos, H., and Patel, N. A. (2014) Transformer 2beta homolog (*Drosophila*) (TRA2B) regulates protein kinase C deltaI (PKCdeltaI) splice variant expression during 3T3L1 preadipocyte cell cycle. *J Biol Chem* 289, 31662-31672.

Figure 4:
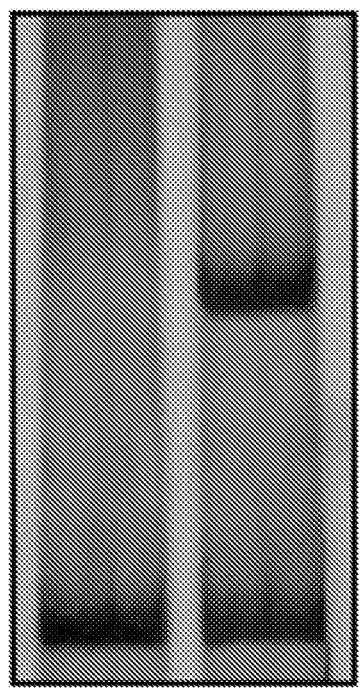
FIG. 4 shows an image of the results from an REMSA demonstrating GAS5 transcript binding to compound G5-1397 (n=3).

Briefly, GAS5 was cloned in TOPO vector which has the T7 promoter. In vitro transcription assay was performed with biotin-label using RiboScribe kit using T7 RNA polymerase at 37° C. for 2 h in the presence of nucleotides, RNase inhibitor, and 5× transcription buffer. 0.1 nM of transcribed, biotin-labeled GAS5 was incubated with 10 nM G5-1397 in presence of 10U yeast tRNA and 10 units of RNase inhibitor in a final volume of 10 µl of RNA shift buffer for 20 min at room temperature and detected using Biotin Chromogenic Detection kit (ThermoFisher). The results with RNA-EMSA demonstrate that G5-1397 bound to GAS5 transcript (FIG. 4). Using the same assay, compounds according to Formulas 4-19 were also observed to bind GAS5 long non-coding RNA.

We claim:

1. A compound have a structure according to Formula 1,

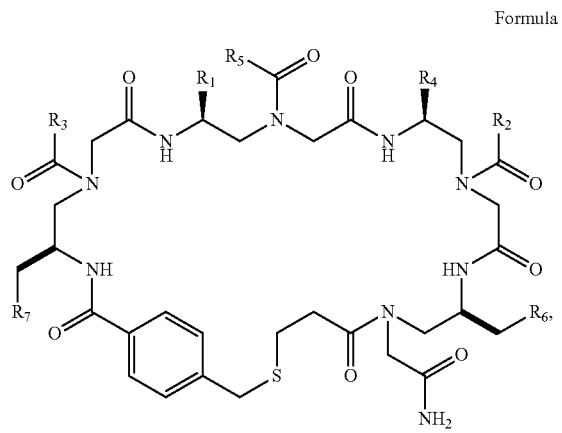

Formula 1 wherein $R_1$ is a methyl, an isobutane, a phenyl, an indole, or a butanamine, wherein $R_2$ is an ethylbenzene, an ethylcyclohexane, an isopentane, a phenyl, a propanamine, or a methylcyclopropane, wherein $R_3$ is a methylcyclopropane, a propionic acid, an ethylbenzene, or a propanamine, wherein $R_4$ is a butanamine, a propionic acid, or a phenyl, wherein $R_5$ is a methylcyclopropane, a propionic acid, or an ethylbenzene, wherein $R_6$ is a phenyl, a propionic acid, an isobutene, and wherein $R_7$ is a phenyl, a propionic acid, a butanamine, or a methyl, and the structure is selected from the group consisting of the structure of Formula 3

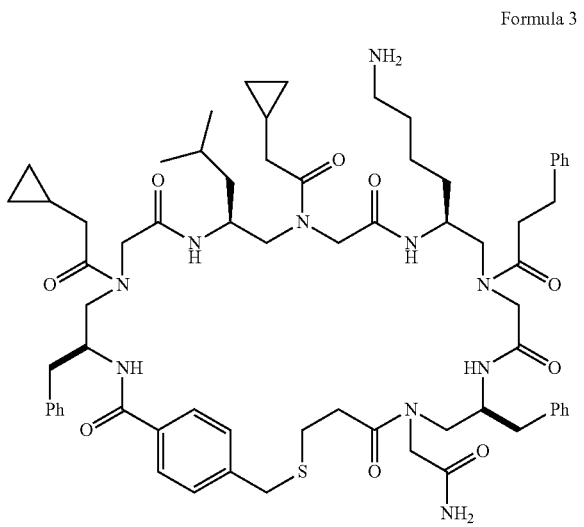 [SMILES: CC(C)C[C@H]1CN(C(=O)CC2CC2)CC(=O)N[C@@H](CCCCN)CN(C(=O)CCc2ccccc2)CC(=O)N[C@@H](Cc2ccccc2)CN(CC(N)=O)C(=O)CCSCc2ccc(cc2)C(=O)N[C@@H](Cc2ccccc2)CN(C(=O)CC2CC2)CC(=O)N1]

Formula 3 and the structure of Formula 14

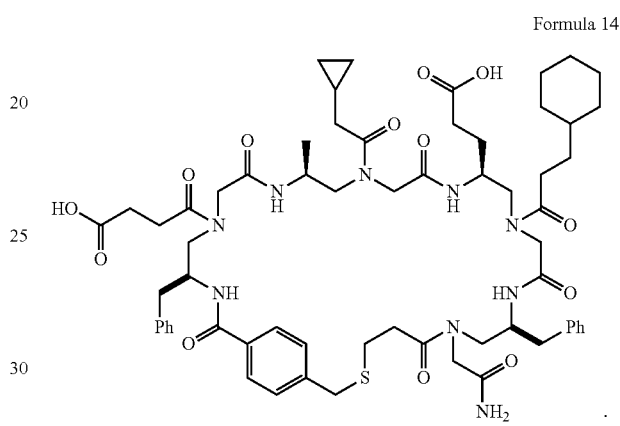

Formula 14

2. The compound of claim 1, wherein the compound is capable of binding GAS5 long non-coding RNA.

3. The compound of claim 2, wherein the GAS5 long non-coding RNA has a sequence about 90%-100% identical to SEQ ID NO. 1.

4. A pharmaceutical formulation comprising:
   (A) a compound having a structure according to Formula 1

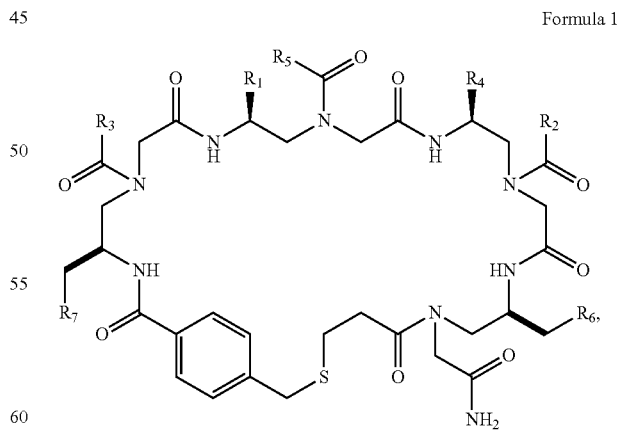

Formula 1 wherein $R_1$ is a methyl, an isobutane, a phenyl, an indole, or a butanamine, wherein $R_2$ is an ethylbenzene, an ethylcyclohexane, an isopentane, a phenyl, a propanamine, or a methylcyclopropane, wherein R₃ is a methylcyclopropane, a propionic acid, an ethylbenzene, or a propanamine,
wherein R₄ is a butanamine, a propionic acid, or a phenyl,
wherein R₅ is a methylcyclopropane, a propionic acid, or an ethylbenzene,
wherein R₆ is a phenyl, a propionic acid, an isobutene, and
wherein R₇ is a phenyl, a propionic acid, a butanamine, or a methyl;
and
the structure is selected from the group consisting of the structure of Formula 3

Formula 3

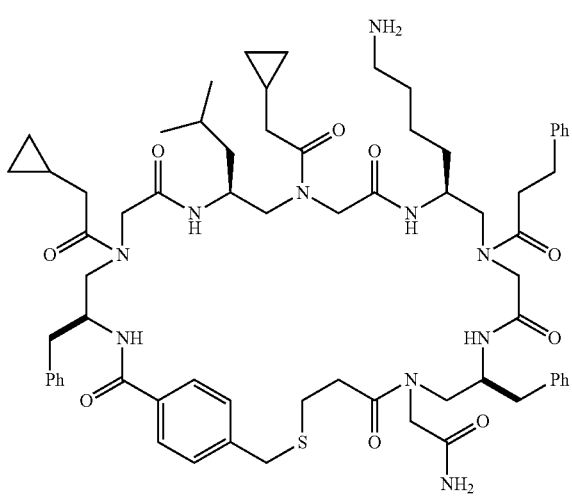

and the structure of Formula 14

Formula 14

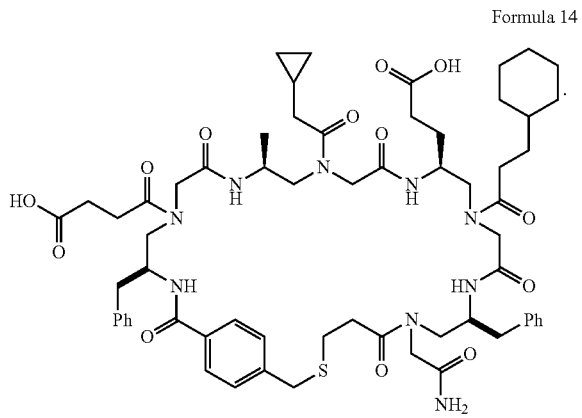 [SMILES: C[C@H]1CN(C(=O)CC2CC2)CC(=O)N[C@@H](CCC(=O)O)CN(C(=O)CCC2CCCCC2)CC(=O)N[C@@H](Cc2ccccc2)CN(CC(N)=O)C(=O)CCSCc2ccc(cc2)C(=O)N[C@@H](Cc2ccccc2)CN(C(=O)CCC(=O)O)CC(=O)N1]

and
(B) a pharmaceutically acceptable carrier.

5. The pharmaceutical formulation of claim 4, wherein the compound is capable of binding a GAS5 long non-coding RNA and wherein the GAS5 long non-coding RNA has a sequence that is 90%-100% identical to SEQ ID NO. 1.

6. The pharmaceutical formulation of claim 4, further comprising an agent selected from the group consisting of: antisense or RNA interference molecules, chemotherapeutics, antineoplasic agents, hormones, antibiotics, antivirals, immunomodulating agents, antinausea, pain modifying agents, anti-inflammatory agents, antipyretics, antibiotics, and/or antibodies or fragments thereof.

7. The compound of claim 1 having the structure of formula 3

Formula 3

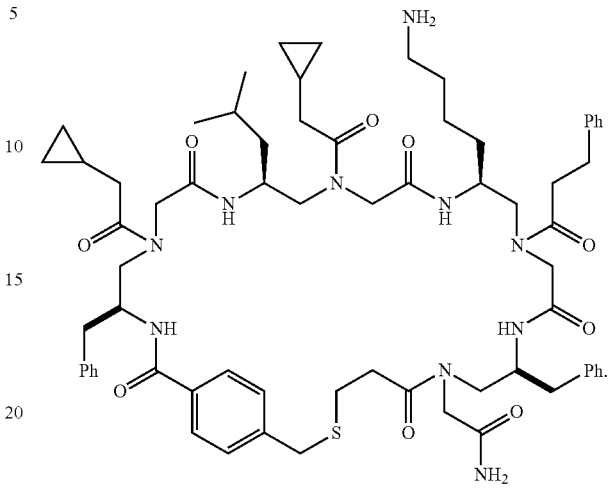

8. The compound of claim 1 having the structure of formula 14

Formula 14

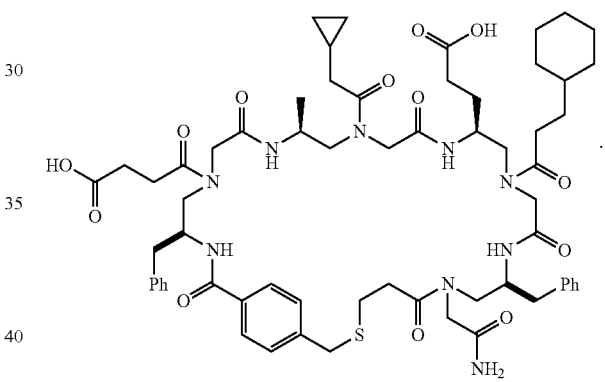

9. The pharmaceutical formulation of claim 4 having the structure of formula 3

Formula 3

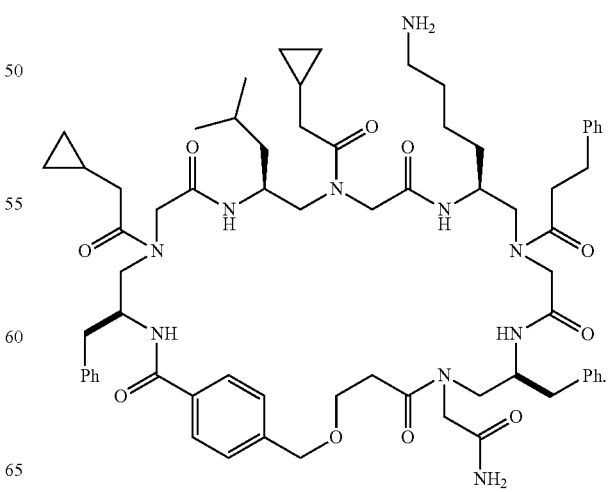

10. The pharmaceutical formulation of claim 4 having the structure of formula 14
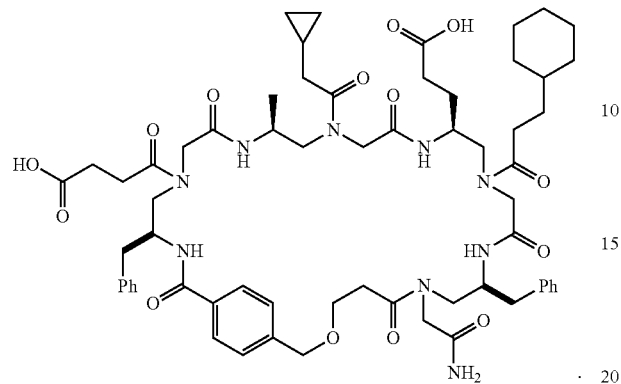
Formula 3B
* * * * *